United States Patent
Jones et al.

(10) Patent No.: US 11,089,747 B2
(45) Date of Patent: Aug. 17, 2021

(54) BIOREACTOR

(71) Applicant: University of Guelph, Guelph (CA)

(72) Inventors: Andrew Maxwell Phineas Jones, Elora (CA); Kevin Frank Piunno, Guelph (CA); Mukund Shukla, Guelph (CA)

(73) Assignee: University of Guelph, Guelph (CA)

( * ) Notice: Subject to any disclaimer, the term of this patent is extended or adjusted under 35 U.S.C. 154(b) by 475 days.

(21) Appl. No.: 16/002,053

(22) Filed: Jun. 7, 2018

(65) Prior Publication Data

US 2018/0352762 A1    Dec. 13, 2018

Related U.S. Application Data

(60) Provisional application No. 62/516,800, filed on Jun. 8, 2017.

(51) Int. Cl.
*A01G 31/06* (2006.01)
*A01G 31/02* (2006.01)
(Continued)

(52) U.S. Cl.
CPC ........... *A01G 31/06* (2013.01); *A01G 9/0297* (2018.02); *A01G 9/06* (2013.01); *A01G 9/24* (2013.01);
(Continued)

(58) Field of Classification Search
CPC ............. A01G 31/06; A01G 9/16; A01G 9/24
See application file for complete search history.

(56) References Cited

U.S. PATENT DOCUMENTS 1,231,976 A * 7/1917 Weitzel, II ............. F16K 31/22
                                                                137/432
3,868,787 A   3/1975 Wong, Jr.
(Continued)

FOREIGN PATENT DOCUMENTS

EP       3069591 A1    9/2016
WO    1994022290 A1   10/1994
(Continued)

OTHER PUBLICATIONS

Shukla et al., Application of 3D printing to prototype and develop novel plant tissue culture systems, Plant Methods—BioMed Central, Jan. 19, 2017, https://plantmethods.biomedcentral.com/articles/10.1186/s13007-017-0156-8.
(Continued)

*Primary Examiner* — Monica L Barlow
(74) *Attorney, Agent, or Firm* — Bereskin & Parr LLP/S.E.N.C.R.L, S.R.L.

(57) ABSTRACT

A bioreactor includes a bioreactor container, and a root stand. The container has a base and one or more sidewalls connected to the base, the base and sidewalls together defining an interior bioreactor volume. The root stand is supported by the container within the bioreactor volume, and includes a first support comb and a second support comb, each support comb having a plurality of spaced apart teeth. The teeth of the first support comb extend in length in a first direction and the teeth of the second support comb extend in length in a second direction different from the first direction. The first support comb overlaying the second support comb when the root stand is supported in the container, and the first support comb being separable from the second support comb when the root stand is removed from the container. A gravity well and atmosphere control container are also disclosed.

5 Claims, 16 Drawing Sheets

(51) Int. Cl.
*A01G 9/029* (2018.01)
*A01G 9/06* (2006.01)
*A61L 2/08* (2006.01)
*A01G 9/24* (2006.01)
*A01G 27/02* (2006.01)
*A61L 2/04* (2006.01)
*A01G 24/00* (2018.01)
*A01G 7/02* (2006.01)
*A01G 31/00* (2018.01)

(52) U.S. Cl.
CPC ............ *A01G 27/02* (2013.01); *A01G 31/02* (2013.01); *A61L 2/04* (2013.01); *A61L 2/081* (2013.01); *A01G 7/02* (2013.01); *A01G 24/00* (2018.02); *A01G 2031/006* (2013.01); *A61L 2202/23* (2013.01)

(56) References Cited

U.S. PATENT DOCUMENTS

| | | | |
|---|---|---|---|
| 4,312,152 A | 1/1982 | Drury et al. | |
| 4,355,484 A | 10/1982 | Mandish | |
| 4,531,324 A | 7/1985 | Yang et al. | |
| 4,586,288 A | 5/1986 | Walton | |
| 4,805,342 A * | 2/1989 | Jenkins | A01G 27/003 47/79 |
| 4,960,703 A | 10/1990 | Paques et al. | |
| 5,097,626 A * | 3/1992 | Mordoch | A01G 27/04 47/48.5 |
| 5,215,920 A | 6/1993 | Lyman et al. | |
| 5,389,542 A | 2/1995 | Teng et al. | |
| 5,906,941 A | 5/1999 | Shetty | |
| 5,914,264 A | 6/1999 | Korman | |
| 7,531,350 B2 | 5/2009 | Shiau | |
| 9,661,844 B2 * | 5/2017 | Aulisa | B30B 11/34 |
| 2012/0137581 A1 * | 6/2012 | Teasdale | A01G 9/0297 47/66.6 |
| 2013/0205662 A1 * | 8/2013 | Yancey | A01G 27/02 47/66.6 |
| 2014/0115958 A1 * | 5/2014 | Helene | A01G 31/06 47/17 |
| 2014/0318012 A1 * | 10/2014 | Fujiyama | A01G 31/02 47/62 R |
| 2014/0338261 A1 * | 11/2014 | Sykes | A01G 31/06 47/62 A |
| 2016/0165821 A1 * | 6/2016 | Fujiyama | A01G 31/06 47/60 |
| 2017/0094914 A1 * | 4/2017 | Paquette | F21V 14/006 |
| 2017/0105368 A1 * | 4/2017 | Mehrman | A01G 27/005 |
| 2018/0007845 A1 * | 1/2018 | Martin | A01G 9/246 |
| 2018/0242531 A1 * | 8/2018 | Berry, III | A01G 27/02 |
| 2018/0325055 A1 * | 11/2018 | Krakover | A01G 31/06 |
| 2019/0223395 A1 * | 7/2019 | Warrick | C02F 1/001 |

FOREIGN PATENT DOCUMENTS

| | | |
|---|---|---|
| WO | 2012044239 A1 | 4/2012 |
| WO | 2016092098 A1 | 6/2016 |
| WO | 2016137223 A2 | 9/2016 |
| WO | 2016137223 A3 | 10/2016 |

OTHER PUBLICATIONS

English machine translation of WO2016137223A2 published as of Jan. 9, 2016.

* cited by examiner

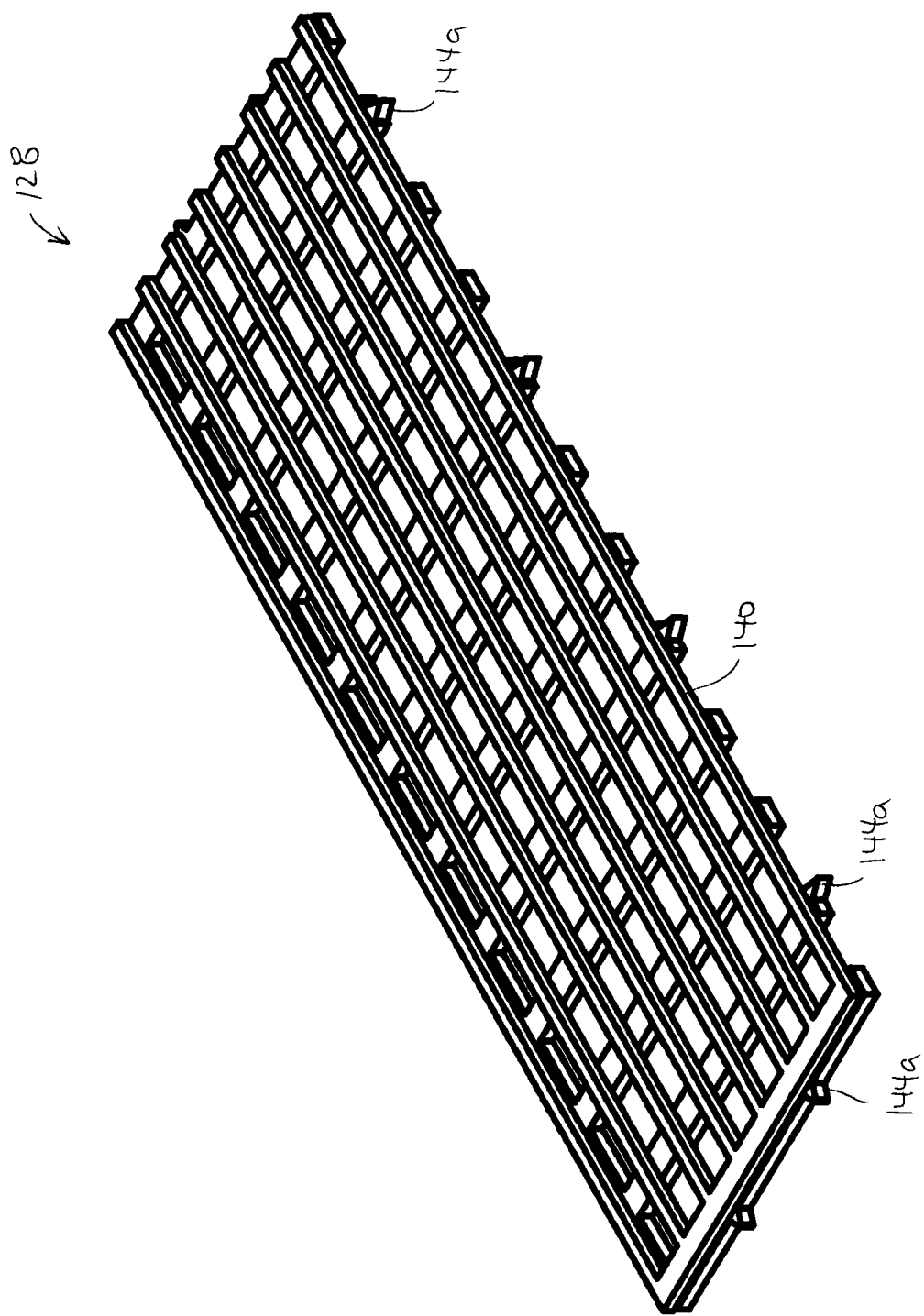

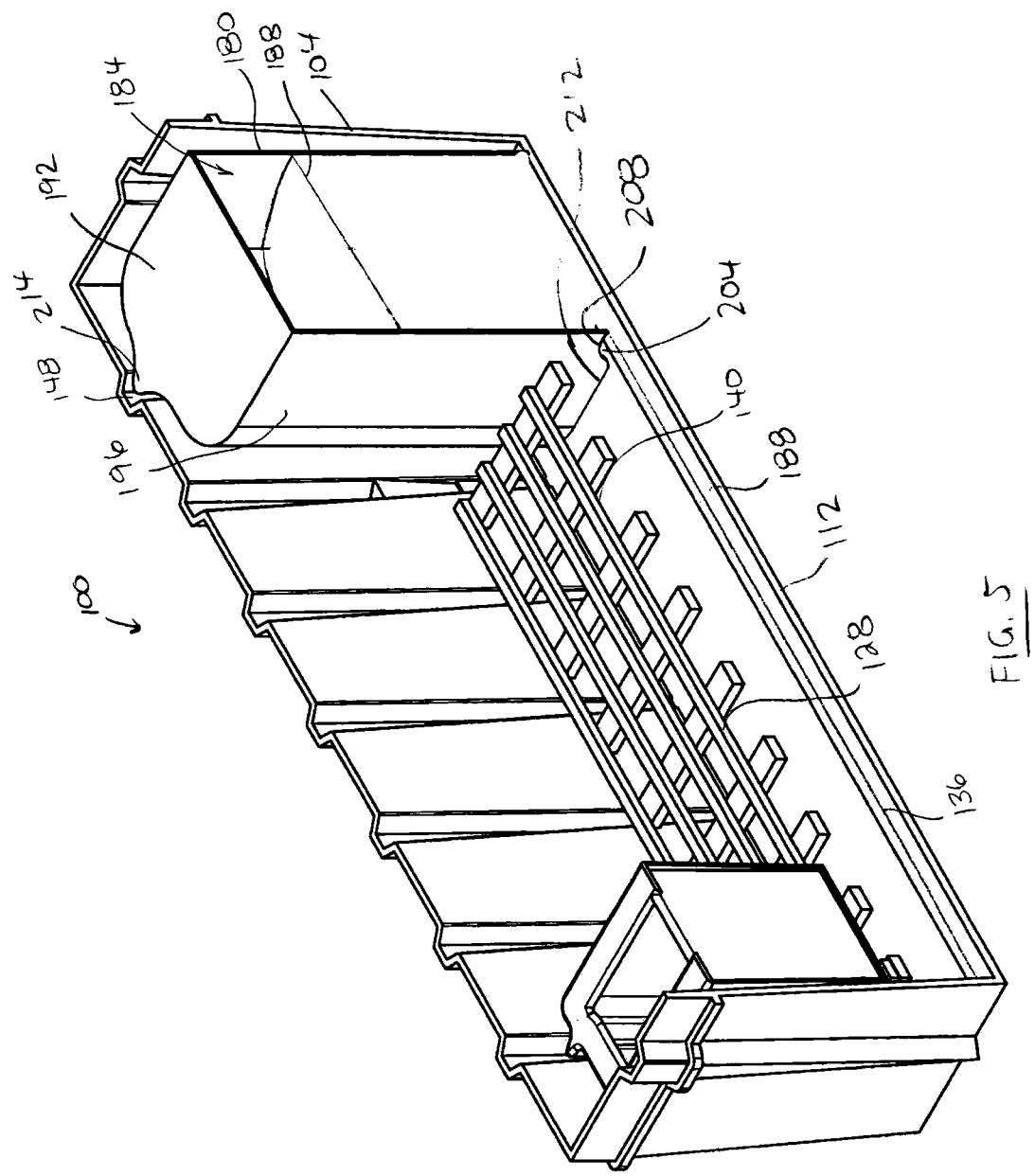

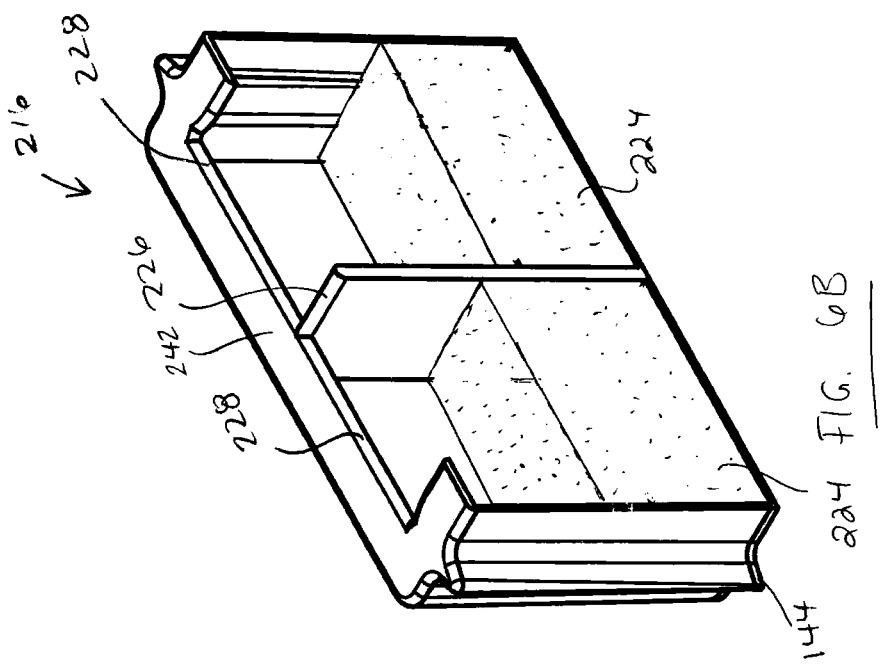
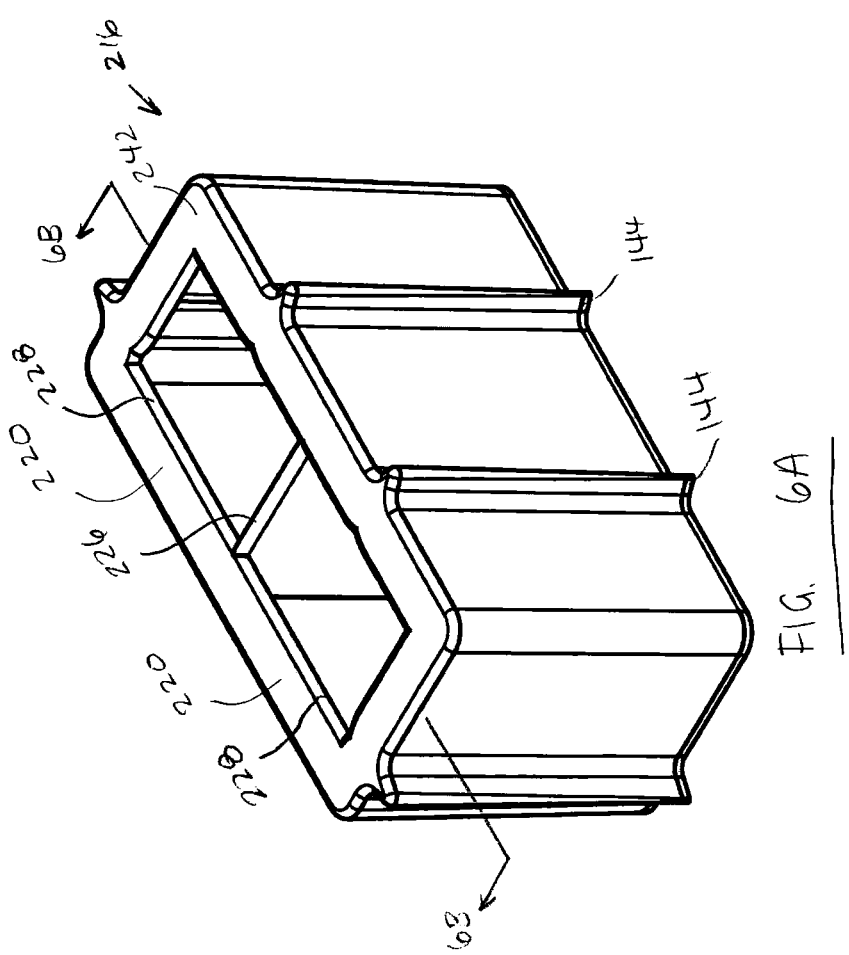

BIOREACTOR

This application claims the benefit of Provisional Application Ser. No. 62/516,800, filed Jun. 8, 2017, which is hereby incorporated herein by reference.

FIELD

This application relates to the field of bioreactors.

INTRODUCTION

A bioreactor is a device that supports an environment conducive to biological growth. In some cases, a bioreactor may include a vessel that holds biological material, such as plants or tissues. The bioreactor may provide a fertile atmosphere for the growth and/or multiplication of the biological material.

DRAWINGS

FIG. 4 is a perspective view of a root stand;

FIG. 5 is a perspective view of the bioreactor of FIG. 3A that has been sectioned along line 5-5 in FIG. 3A;

FIG. 6A is a perspective view of an atmospheric control container in accordance with an embodiment;

FIG. 6B is a perspective view of the atmospheric control container of FIG. 6A that has been sectioned along line 6B-6B in FIG. 6A;

SUMMARY

Figure 1A:
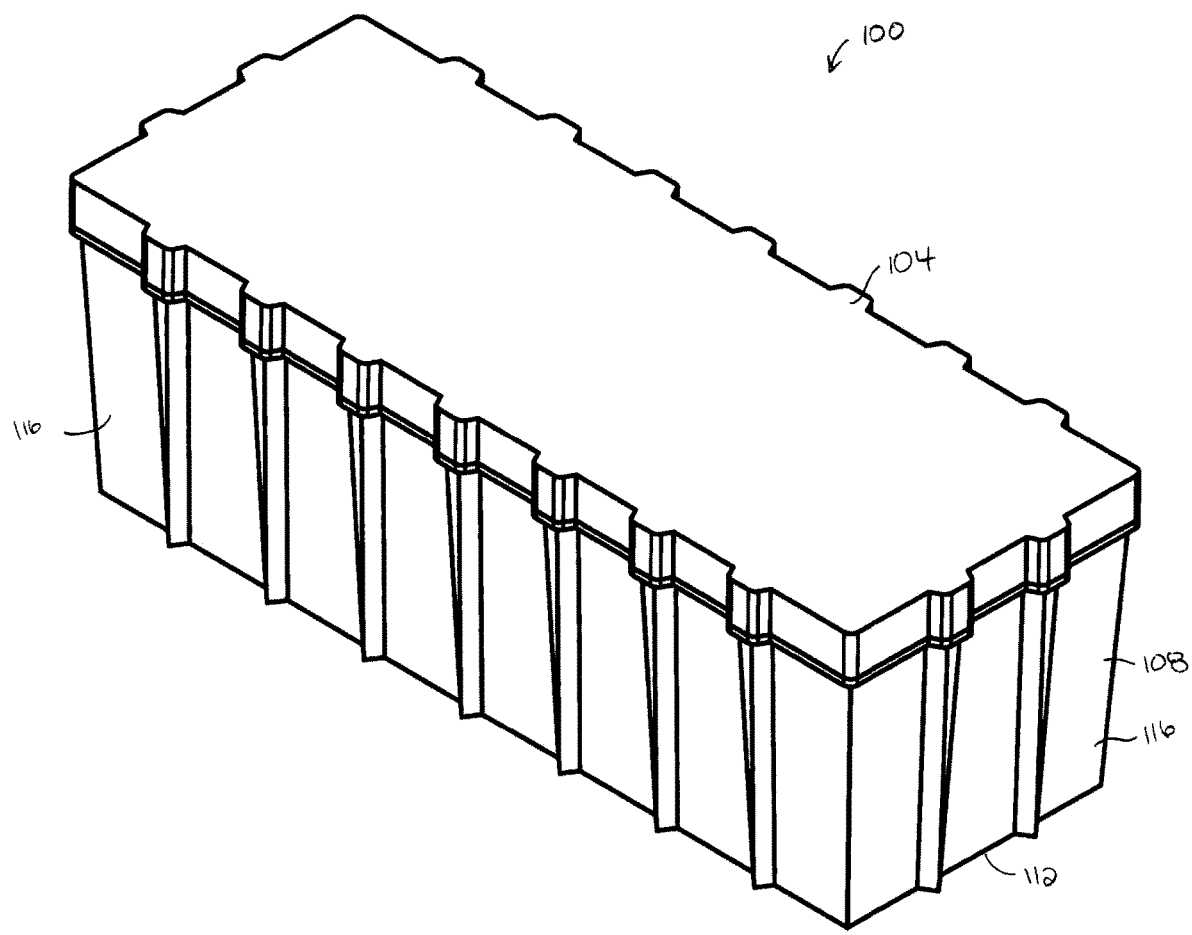
FIG. 1A is a perspective view of a bioreactor in accordance with an embodiment.

In one aspect, a method of sterilizing a plurality of bioreactor containers is provided. The method includes nesting the plurality of bioreactor containers into a stack; connecting a lid to a first bioreactor container of the plurality of bioreactor containers, the first bioreactor container having bioreactor sidewalls, and the lid inhibiting both inward and outward deflection of the container sidewalls; placing the stack with the connected lid into an autoclave; and operating the autoclave to sterilize the stack of nested bioreactor containers substantially simultaneously.

In another aspect, a method of sterilizing a bioreactor is provided. The method includes nesting a plurality of bioreactor containers into a stack, each bioreactor container except an uppermost bioreactor container receiving at least 50% of a bioreactor container above; connecting a lid to the uppermost bioreactor container, the uppermost bioreactor container having sidewalls, and the lid inhibiting both inward and outward deflection of the sidewalls; placing the stack with the connected lid into an autoclave; and operating the autoclave to sterilize the stack of nested bioreactor containers substantially simultaneously.

In another aspect, a bioreactor is provided. The bioreactor includes a bioreactor container and a root stand. The bioreactor container has a base and one or more sidewalls connected to the base, the base and sidewalls together defining an interior bioreactor volume. The root stand is supported by the container within the bioreactor volume, and includes a first support comb and a second support comb. Each support comb has a plurality of spaced apart teeth. The teeth of the first support comb extend in length in a first direction and the teeth of the second support comb extend in length in a second direction different from the first direction. The first support comb overlay the second support comb when the root stand is supported in the container. The first support comb is separable from the second support comb when the root stand is removed from the container.

In another aspect, a bioreactor is provided. The bioreactor includes a bioreactor container and a gravity well. The bioreactor container has a base and one or more sidewalls connected to the base. The base and sidewalls together define an interior bioreactor volume. The gravity well is supported by the container within the bioreactor volume. The gravity well has an upper wall, one or more sidewalls extending downwardly from the upper wall, and one or more liquid outlets at a lower end of the gravity well. The one or more liquid outlets defining a liquid level of the bioreactor container. The upper wall and sidewalls together define an interior reservoir volume that is sealed except for the one or more liquid outlets.

DESCRIPTION OF VARIOUS EMBODIMENTS

Numerous embodiments are described in this application, and are presented for illustrative purposes only. The described embodiments are not intended to be limiting in any sense. The invention is widely applicable to numerous embodiments, as is readily apparent from the disclosure herein. Those skilled in the art will recognize that the present invention may be practiced with modification and alteration without departing from the teachings disclosed herein. Although particular features of the present invention may be described with reference to one or more particular embodiments or figures, it should be understood that such features are not limited to usage in the one or more particular embodiments or figures with reference to which they are described.

The terms "an embodiment," "embodiment," "embodiments," "the embodiment," "the embodiments," "one or more embodiments," "some embodiments," and "one embodiment" mean "one or more (but not all) embodiments of the present invention(s)," unless expressly specified otherwise.

The terms "including," "comprising" and variations thereof mean "including but not limited to," unless expressly specified otherwise. A listing of items does not imply that any or all of the items are mutually exclusive, unless expressly specified otherwise. The terms "a," "an" and "the" mean "one or more," unless expressly specified otherwise.

As used herein and in the claims, two or more parts are said to be "coupled", "connected", "attached", "joined" or "fastened" where the parts are joined or operate together either directly or indirectly (i.e., through one or more intermediate parts), so long as a link occurs. As used herein and in the claims, two or more parts are said to be "directly coupled", "directly connected", "directly attached", "directly joined", or "directly fastened" where the parts are connected in physical contact with each other. As used herein, two or more parts are said to be "rigidly coupled", "rigidly connected", "rigidly attached", "rigidly joined", or "rigidly fastened" where the parts are coupled so as to move as one while maintaining a constant orientation relative to each other. None of the terms "coupled", "connected", "attached", "joined", and "fastened" distinguish the manner in which two or more parts are joined together.

As used herein and in the claims, a first element is said to be "received" in a second element where at least a portion of the first element is received in the second element unless specifically stated otherwise.

Figure 1B:
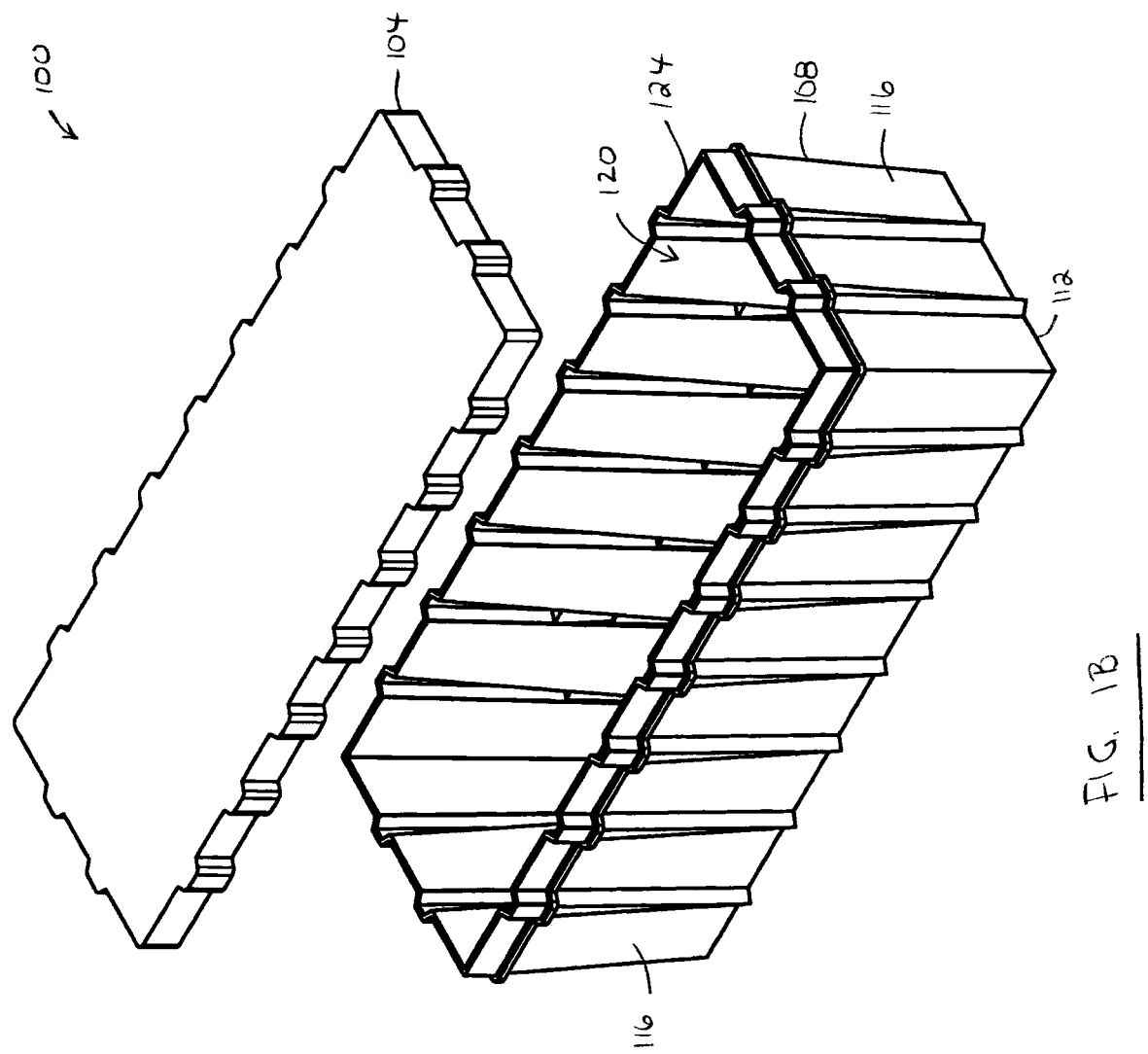
FIG. 1B is a perspective view of the bioreactor of FIG. 1A with a bioreactor lid removed.

FIGS. 1A-1B show a bioreactor 100 in accordance with an embodiment. Bioreactor 100 provides a sealed sterile environment for multiplying biological material, such as plants, into viable specimens that can survive to maturity outside of the bioreactor. For example, bioreactor 100 may produce dozens of plants (e.g. fruit plants, vegetable plants, or flowers) that may be transplanted into fields or greenhouses and grown to maturity.

Bioreactor 100 includes a container 104 and a lid 108. Bioreactor container 104 includes a base 112 and one or more sidewalls 116 that collectively define an interior volume 120. Bioreactor container 104 has an opening 124 which can be closed by removable bioreactor lid 108. In the illustrated example, container opening 124 is located at an upper end of bioreactor container 104 and delimited by bioreactor sidewalls 116. When container opening 124 is closed by bioreactor lid 108, bioreactor volume 120 may be substantially liquid and gas sealed against the outside environment.

Bioreactor container 104 can have any shape suitable for growing biological material, such as plants for example. In the illustrated example, bioreactor container 104 is substantially frusto-pyramidal, having four sidewalls 116 extending upwardly and outwardly from a common base 112 to container opening 124. In other embodiments, bioreactor container 104 may be parallelepiped (e.g. cuboid), or another regular or irregular shape. For example, bioreactor container 104 may be cylindrical (e.g. having one sidewall extending from a circular base) or spherical (e.g. having a lower portion defining a base and an upper portion defining a sidewall).

Bioreactor container 104 can be formed of any material suitable for holding biological material (e.g. plants) and associated nutrient medium (e.g. liquid or gel). This may require bioreactor container 104 to be liquid or gel impervious, at least where the liquid or gel makes contact with the bioreactor container 104. For example, at least container base 112 and a lower portion of container sidewalls 116 may be liquid and/or gel impervious. In some embodiments, all walls of bioreactor container 104 are entirely liquid impervious, or liquid and gas impervious. This may help to prevent the passage of gas and/or humidity between the environment and the bioreactor volume 120. For example, bioreactor container 104 may be made of plastic (e.g. ABS or polycarbonate), glass, ceramic, or metal.

Bioreactor container 104 may be formed of a material that can withstand high temperature sterilization in an autoclave (e.g. exceeding 120° C.). For example, bioreactor container 104 may be made of a plastic material having a glass transition temperature exceeding 120° C. (e.g. polycarbonate). In other embodiments, bioreactor container 104 may be produced as a single-use vessel out of a disposable material that is sterilized by gamma radiation, for example.

Bioreactor container 104 may be formed of an opaque, translucent, or substantially transparent material. A transparent or translucent bioreactor container 104 may allow the plants inside to receive light radiation required to promote growth from sources of light outside of bioreactor 100. This can allow several bioreactors 100 to share a common exterior light source. An opaque bioreactor container 104 may block exterior light sources so that the light exposure to the plants inside is strictly determined by lighting provided interior to bioreactor 100. For example, bioreactor 100 may include one or more light sources integrated into bioreactor lid 108, which shine light radiation onto the plants in bioreactor volume 120 below. This can allow greater control over the light radiating the plants to optimize plant growth.

Bioreactor container 104 can have any size suitable for growing plants into viable specimens for transplanting (e.g. in a field or greenhouse). In the illustrated embodiment, bioreactor container 104 has a bioreactor volume 120 of 1.44 L. In other embodiments, bioreactor container 104 may have a bioreactor volume 120 of between 500 mL and 15 L.

In use, plants are placed into bioreactor 100 along with a nutrient medium. The nutrient medium may be a liquid (e.g. water-based medium), or a gel (e.g. agar-based medium). A gel medium may have sufficient viscosity to hold the plants upright, with the roots in the medium and the leaves above the medium. This allows the roots to receive the nutrients required for delivery up the stem of the plant, and exposes the leaves to air and light radiation. However, gel mediums can be expensive, require increased labour, and can lead to root damage upon transplantation, which can affect the business case for their use in bioreactors for propagating lower-value plants.

Liquid nutrient-media have insufficient viscosity to hold plants upright. As a result, the plants may lie on their side submerging a portion of the roots and leaves in the nutrient medium. The base of the plants may lack access to the nutrient medium/rooting hormones and the submerged leaves have reduced exposure to gas and light radiation. Consequently, plant growth and root induction is suboptimal. To improve plant growth in liquid nutrient media, the bioreactor may be mounted to a rocker that tilts the bioreactor from side-to-side, periodically collecting the liquid at one side of the bioreactor and then the other. This subjects the plantlets to continuously variable medium depth and is referred to as a temporary immersion bioreactor system.

During shallow/dry periods the plant tissues may be better exposed to the headspace of the vessel to facilitate gas exchange, and during deep periods the roots may be better exposed to the nutrient medium. While rockers can be effective for improving plant growth with liquid nutrient media, they are expensive which may again affect the business case for their use in bioreactors for propagating lower-value plants.

Figure 2B:
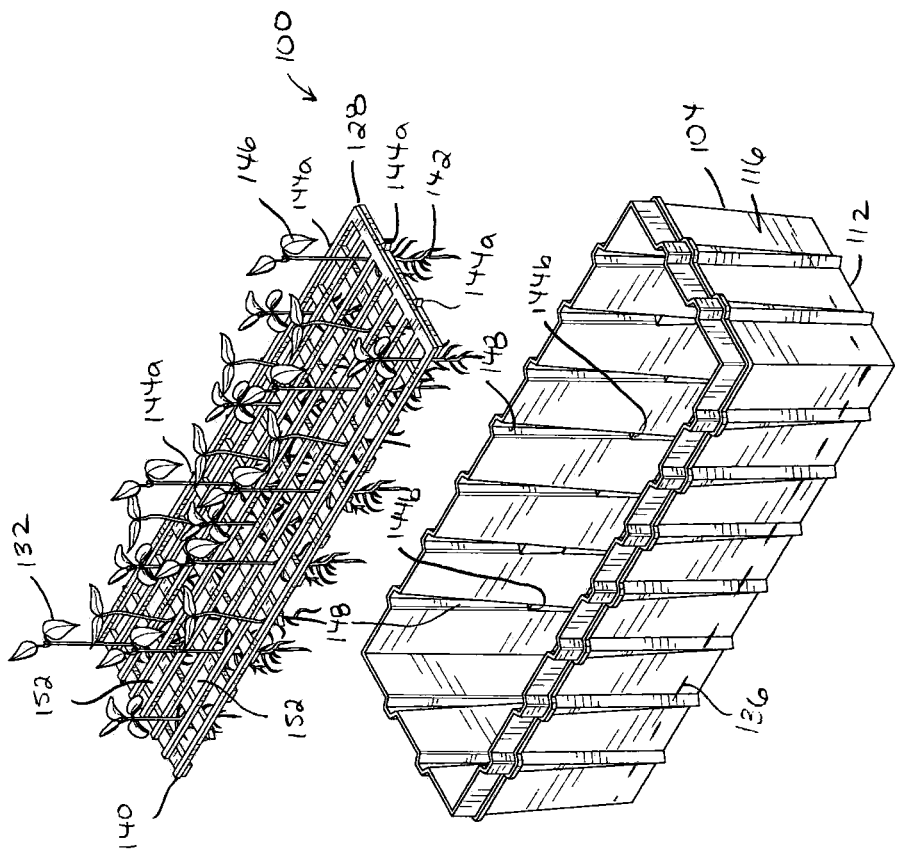
FIG. 2B is a perspective view of the bioreactor of FIG. 2A with the root stand and plants removed.
Figure 2A:
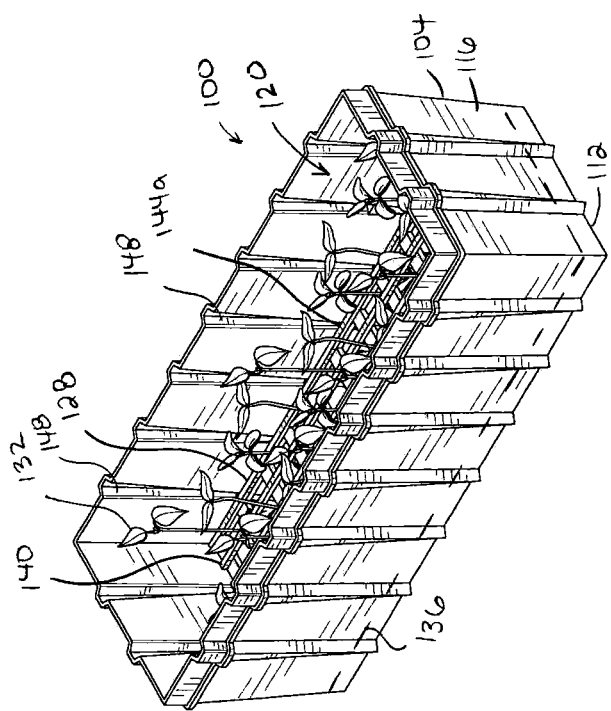
FIG. 2A is a perspective view of the bioreactor of FIG. 1A holding a root stand carrying a plurality of plants, in accordance with an embodiment.

Reference is now made to FIGS. 2A-2B, which show bioreactor 100 including a root stand 128 supporting plants 132 in upright positions. Root stand 128 provides support to hold plants 132 in an upright position, which can allow a cost-effective liquid nutrient medium to be used with or without a rocker system. Of course, in some circumstances, a rocker system may still be used to obtain certain growth objectives. Referring to FIGS. 2A-2B and 3A-3B, root stand 128 is supported in bioreactor container 104 with a root support structure 140 spaced apart from container base 112 at or above nutrient medium level 136. This allows the roots 142 to extend downward from the root support structure 140 into the nutrient medium below, and for the leaves 146 to extend above the root support structure 140 for exposure to air and light radiation. In the result, bioreactor 100 including root stand 128 may mitigate the disadvantages of liquid nutrient media that cannot support plants in an upright position and allow for increased plant density due to their vertical orientation.

Root stand 128 may be supported in bioreactor container 104 in any manner that holds root support structure 140 spaced apart from container base 112. At least one of bioreactor container 104 and root stand 128 may include an abutment portion 144 which makes contact with the other of bioreactor container 104 and root stand 128 to hold root support structure 140 above container base 112. Abutment portions 144 can take any form suitable for collectively supporting root support structure 140 above container base 112. In the illustrated embodiment, root stand 128 includes abutment portions 144a (see also FIG. 4) which protrude outwardly from root support structure 140 and which seat onto abutment portions 144b of container sidewalls 116. As shown, container abutment portions 144b may be formed as shelves having an upper surface that supports stand abutment portions 144a. Each abutment portion 144b may be situated within a sidewall groove 148. Stand abutment portions 144a may be sized, shaped, and arranged to key into sidewall grooves 148, which may provide lateral stability and consistent positioning to root stand 128.

In other embodiments, root stand 128 may include abutment members formed as legs (not shown) that extend below root support structure 140 to hold root support structure 140 above container base 112.

Root stand 128 can be made of any material suitable for supporting plants inside a bioreactor container above a volume of nutrient medium. For example, root stand 128 may be made of plastic, glass, ceramic, or metal. In some embodiments, root stand 128 may be substantially non-porous to facilitate easy cleaning. In some embodiments, root stand 128 may be formed of a material that can withstand high temperature sterilization in an autoclave (e.g. exceeding 120° C.). For example, root stand 128 may be made of a plastic material having a glass transition temperature exceeding 120° C. (e.g. polycarbonate).

Root stand 128 may form a lattice having a plurality of spaced apart apertures 152. As shown in FIG. 2B, plants 132 may extend through apertures 152 from below the root support structure 140 to above the root support structure 140. Within apertures 152, plants 132 are afforded lateral stability that promotes an upright position.

Figure 2C:
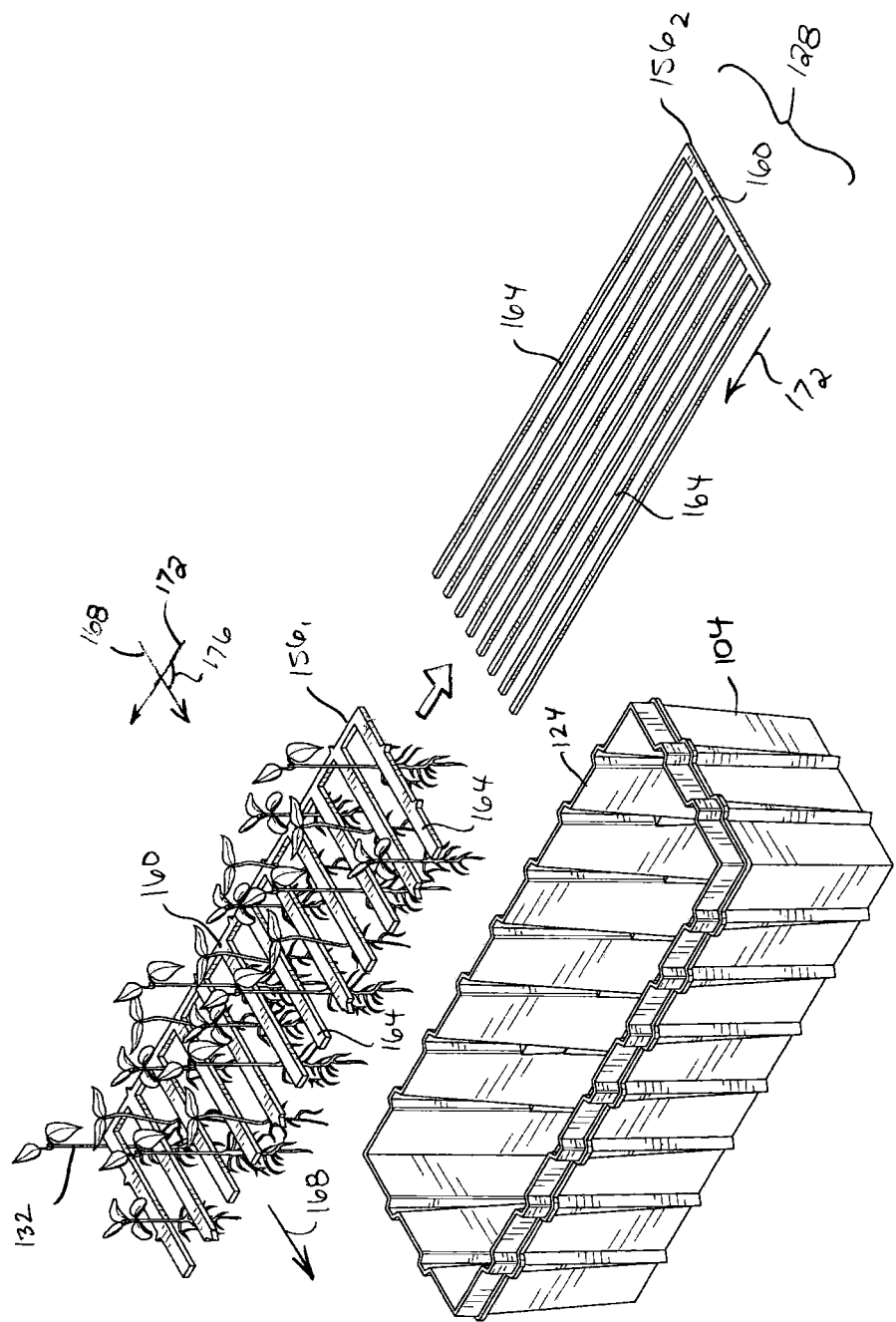
FIG. 2C is a perspective view of the bioreactor of FIG. 2B with one comb of the root stand removed from the plants.
Figure 2D:
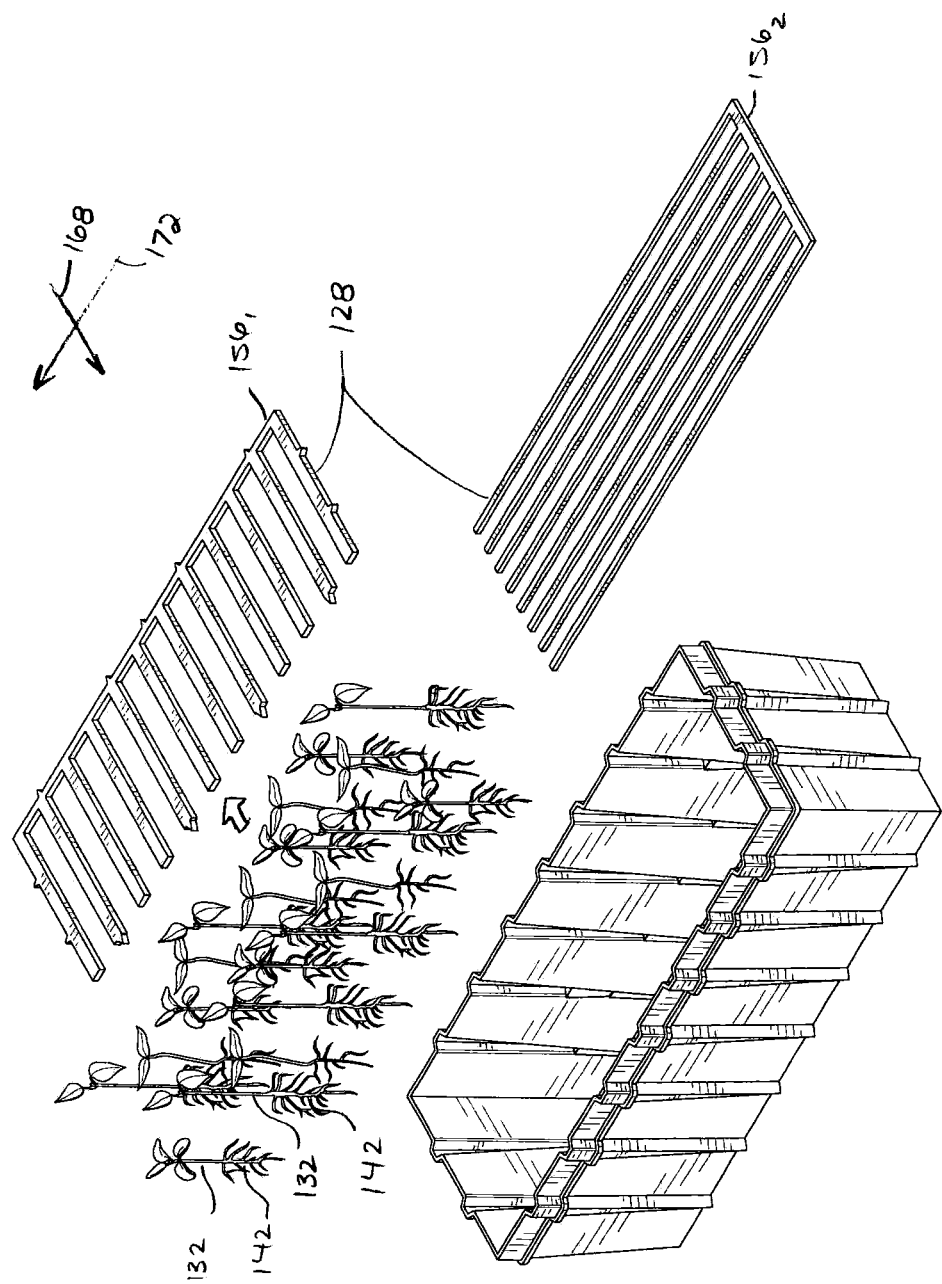
FIG. 2D is a perspective view of the bioreactor of FIG. 2C with both combs removed from the plants.

Turning to FIGS. 2C and 2D, root stand 128 includes first and second combs $156_1$ and $156_2$ which are removably positioned atop each other to form the lattice structure that defines apertures 152 (FIG. 2B). As shown, each comb 156 includes a base 160 and a plurality of parallel, spaced apart teeth 164 extending from the base 160. The teeth 164 of comb $156_1$ extend in a different direction from the teeth 164 of comb $156_2$ so that when the second comb $156_1$ overlays first comb $156_2$, the teeth 164 of the two combs 156 form the crisscrossing lattice shape. Teeth 164 of comb $156_1$ extend in a first direction 168 and teeth 164 of comb $156_2$ extend in a second direction 172. The angle 176 between first and second teeth directions 168 and 172 is preferably large enough to form many apertures 152 (e.g. 10 to 200 apertures). In the illustrated example, angle 176 is 90 degrees. In other embodiments, angle 176 may be between 30 and 150 degrees.

Combs 156 can have any number of teeth suitable to form a lattice with many apertures 152 when overlaid on each other. In the illustrated embodiment, first comb $156_1$ has 12 teeth and second comb $156_2$ has 8 teeth. In other embodiments, combs 156 may have between 5 and 50 teeth, for example. The widest dimension of each aperture 152 (FIG. 2B) is preferably 0.5 mm to 20 mm.

As plants grow on root stand 128, they may become more difficult to remove without damaging the plant. For example, pulling the plant 132 upwardly through the aperture 152 (FIG. 2B) to remove the plant 132 may destroy much of the root structure. In one aspect, root stand 128 may facilitate removal of grown plants 132 damage-free. FIGS. 2A-2D illustrate a method of removing plants 132 from root stand 128, which may avoid damage to the plants 132. In FIG. 2A, the bioreactor lid (not shown) is removed to provide access to the bioreactor volume 120 containing plants 132 and root stand 128. FIG. 2B shows removing root stand 128 with plants 132 attached, out of bioreactor container 104 through container opening 124. FIG. 2C shows moving second comb $156_2$ parallel to second teeth direction 172 away from second comb 156. As shown, the parallel, spaced apart arrangement of teeth 164 allows comb $156_2$ to move in direction 172 without entanglement by plants 132, even if roots 142 are wrapped around teeth 164. Similarly, FIG. 2D shows moving first comb $156_1$ parallel to first direction 168 away from plants 132, thereby completing the separation of plants 132 from root stand 128. In the result, plants 132 are removed without damage. As shown, teeth 164 of the first and/or second combs $156_1$ and $156_2$ may extend substantially linearly in the first and second teeth directions 168 and 172 respectively. Teeth 164 of the first and/or second combs $156_1$ and $156_2$ may extend in length across substantially the dimensions of the interior of the bioreactor container 104 measured parallel to the first and second teeth directions 168 and 172 respectively.

Figure 3A:
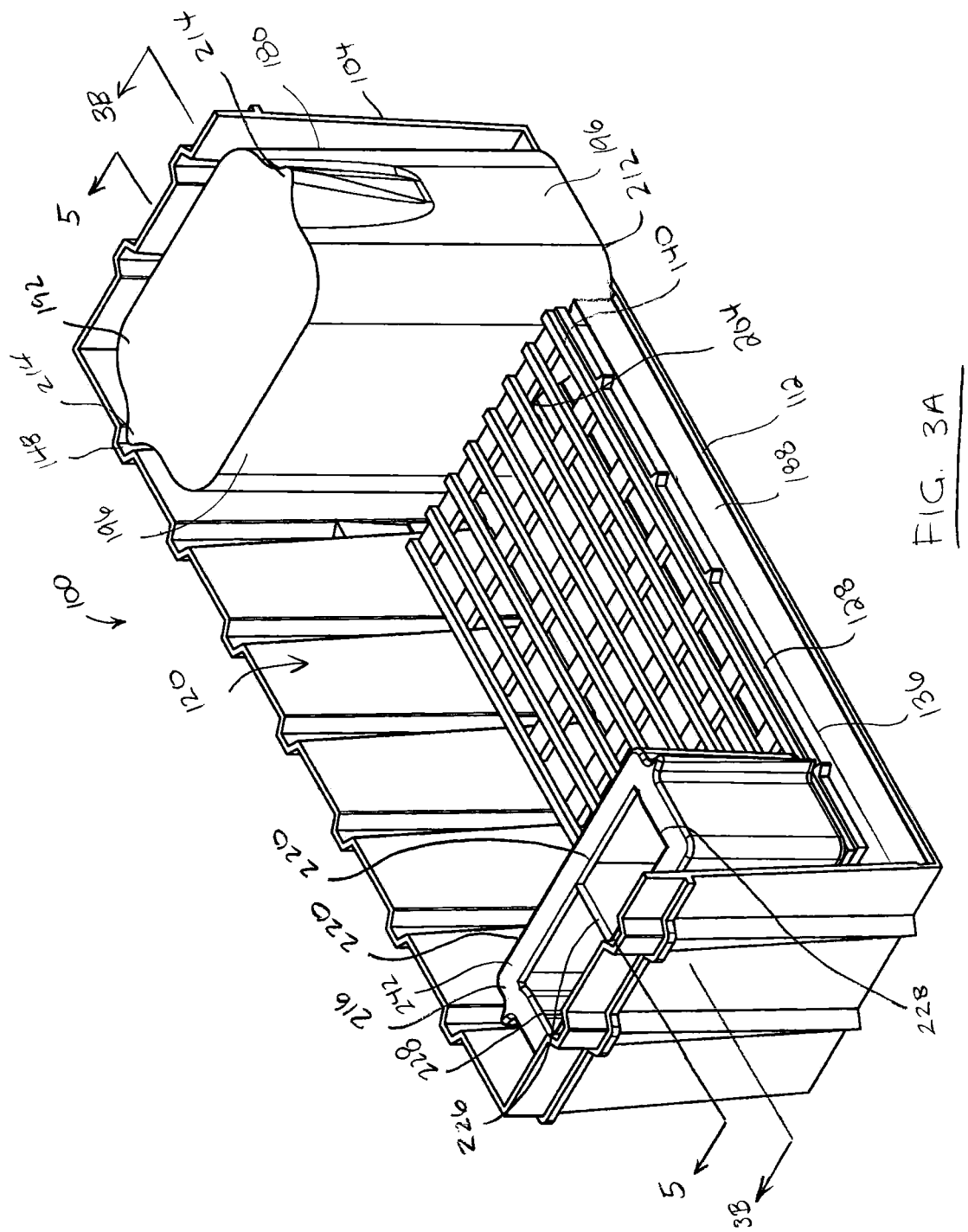
FIG. 3A is a partial cross-sectional view of a bioreactor including a root stand, a gravity well, and an atmospheric control container.
Figure 3B:
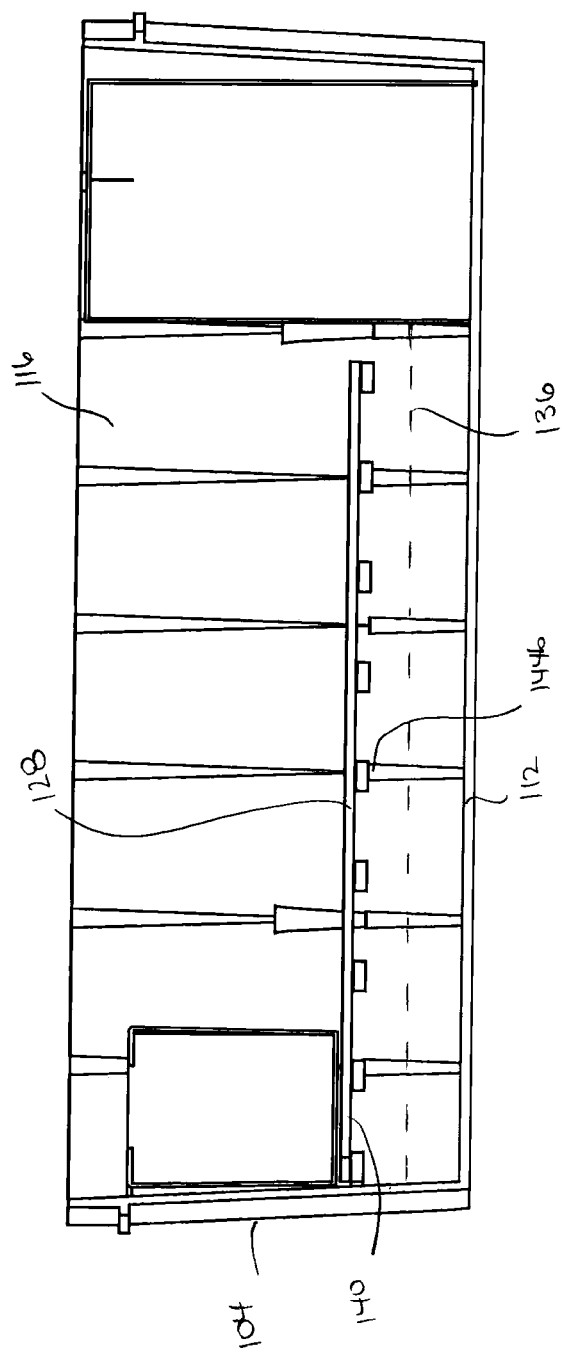
FIG. 3B is a perspective view of the bioreactor of FIG. 3A that has been sectioned along line 3B-3B in FIG. 3A.

Reference is now made to FIGS. 3A and 5. Plants within bioreactor 100 consume nutrient medium as they grow. This may cause the nutrient medium level 136 within bioreactor 100 to fall. Where plants are supported at a fixed height on a root stand 128, a falling nutrient medium level 136 can result in fewer roots being submerged. One option for restoring the nutrient medium level 136 is to open bioreactor 100 and replenish the volume of nutrient medium. However, this may vent the internal atmosphere of the bioreactor container 104 and break the sterile conditions of the bioreactor 100 that promote improved plant growth. Also, manual replenishment may be labor intensive, requiring each bioreactor 100 to be closely monitored and replenished to maintain the nutrient medium depth 136. A facility may contain dozens, hundreds, or even thousands of bioreactors 100.

Another option is to provide bioreactor 100 with a nutrient medium inlet connected to a fluid line, and to pump nutrient medium into bioreactors 100 to maintain the nutrient medium level 136. However, the pumps, depth sensors, and fluid lines associated with such an arrangement could be complex and costly.

In the illustrated embodiment, bioreactor 100 includes a gravity well 180. Gravity well 180 is positionable within bioreactor container 104, and includes a reservoir volume 184 holding nutrient medium 188. The nutrient medium 188 is automatically dispensed from gravity well 180 to maintain the nutrient medium level 136 within bioreactor container 104. As shown, gravity well 180 may be free of electronic parts. Gravity well 180 includes an upper wall 192 and one or more sidewalls 196 which extend downwardly from upper wall 192, and a liquid outlet 204 at a lower end of gravity well 180. The upper wall 192 and sidewalls 196 together define the interior reservoir volume 184. Gravity well 180 may or may not include a bottom wall.

In use, reservoir volume 184 of gravity well 180 is filled with nutrient medium 188 and then gravity well 180 placed into bioreactor container 104. In the illustrated embodiment, gravity well 180 is placed in contact with container base 112. In other embodiments, gravity well 180 is supported above container base 112. Gravity acts on the nutrient medium 188 within reservoir volume 184, which causes nutrient medium 188 to discharge through liquid outlet 204 into bioreactor container 104. Substantially simultaneously, air enters reservoir volume 184 of gravity well 180 through liquid outlet 204 to replace the discharged volume of nutrient medium 188.

When the nutrient medium inside bioreactor container 104 rises to the upper end 208 of liquid outlet 204, air entry into reservoir volume 184 becomes blocked, which stops the discharge of further liquid medium from reservoir volume 184. When the nutrient medium is consumed and inches below the liquid outlet upper end 208, air is again able to enter the reservoir volume 184 concurrently as nutrient medium is discharged from gravity well 180. This pattern of events occurs automatically and repetitively to maintain the nutrient medium level 136 as nutrient medium 188 is consumed by the plants. Thus, the liquid outlet upper end 208 defines the nutrient medium level 136 maintained by gravity well 180.

It will be appreciated that above liquid outlet upper end 208, gravity well 180 is gas tight so that when the nutrient medium level rises to liquid outlet upper end 208 there are no unblocked gas inlets into gravity well 180 and the discharge of nutrient medium 188 is stopped. Gravity well 180 may include a plurality of discrete liquid outlets 204, the uppermost upper end 208 of the liquid outlets 204 defining the nutrient medium liquid level 136.

In one aspect, gravity well 180 may allow for the use of liquid culture without the need for a rocker. Whereas a rocker is commonly used to facilitate gas exchange, the gravity well may facilitate gas exchange by providing a continuous thin layer of liquid medium in which gases naturally diffuse and some of the plant sits above the liquid medium. For example, gravity well 180 may be used for shoot multiplication to promote better multiplication rates than on semi-solid medium, but have no need for a rocker system.

Bioreactor 100 may include a root stand 128, a gravity well 180, or both. As shown, where bioreactor 100 includes both a root stand 128 and a gravity well 180, the liquid outlet upper end 208 may be positioned at or below root support structure 140. This allows gravity well 180 to define a nutrient medium level 136 inside bioreactor container 104 that is at or below root support structure 140.

Gravity well 180 can have any shape suitable for holding nutrient medium inside a reservoir volume. In the illustrated example, gravity well is substantially parallelepiped (e.g. cuboid), having four sidewalls 196 between an upper wall 192 and a lower end 212. In other embodiments, gravity well 180 may be another regular or irregular shape. For example, gravity well 180 may be cylindrical (e.g. having one sidewall extending from a circular upper wall) or spherical (e.g. having an upper portion defining an upper wall and a lower portion defining a sidewall).

In some embodiments, gravity well 180 may be include a protrusion or recess that keys into bioreactor container 104. In the illustrated example, gravity well 180 includes protrusions 214 which key into container sidewall grooves 148. This may provide gravity well 180 with positional stability in bioreactor container 104.

Gravity well 180 can be made of any material that is gas tight so as not to allow gas to enter reservoir volume 184 when the nutrient medium level 136 rises to liquid outlet upper end 208. In some examples, gravity well 180 may be made of plastic, ceramic, glass, or metal.

Gravity well 180 can be any size suitable to fit within bioreactor volume 120, and to store sufficient nutrient medium 188 to supply plants within bioreactor 100 across a complete growth cycle. Preferably, gravity well 180 should be relatively compact so as not to occupy too much space within bioreactor container 104 that could otherwise be used for growing plants. In the illustrated embodiment, gravity well 180 has a reservoir volume 184 of 256 mL. In other embodiments, gravity well 180 may have a reservoir volume 184 of between 50 mL and 1 L, or between 5% and 20% of the bioreactor volume 120.

Reference is now made to FIGS. 3A and 6A-6B. Bioreactor container 104 may be kept sealed from the time the plants are deposited until they are ready to be removed (e.g. for transplanting). Isolation from the outside is required to maintain sterility but can introduce problems with humidity and the composition of the headspace environment. Plant growth may be further improved by moderating the ambient gas conditions (e.g. $CO_2$, ethylene, and relative humidity) within the bioreactor container 104. For example, relative humidity within bioreactor container 104 may tend towards a steady state of close to 100% absent any environmental controls, and this may result in poor growth due to hyperhydricity.

In some embodiments, bioreactor 100 includes an atmospheric control container 216. Bioreactor 100 may include any one or more (or all) of root stand 128, gravity well 180, and atmospheric control container 216. As shown, atmospheric control container 216 may include two or more storage chambers 220 for holding atmospheric control materials 224. The atmospheric control materials 224 act to regulate the proportion of one or more components (e.g. $CO_2$, ethylene, or relative humidity) of the ambient gas within bioreactor container 104.

Examples of atmospheric control materials 224 that influence the steady-state relative humidity within bioreactor container 104 include: sodium chloride, which may promote a steady state relative humidity (at 20° C.) of about 75%; potassium chloride, which may promote a steady state relative humidity (at 20° C.) of about 85%; and potassium nitrate, which may promote a steady state relative humidity (at 20° C.) of about 95%.

Examples of atmospheric control materials 224 that influence the proportion of $CO_2$ within bioreactor container 104 include a mixture of sodium bicarbonate and sodium carbonate in water. The ratio of these chemicals in influences the rate that $CO_2$ is evolved from the solution.

Examples of atmospheric control materials 224 that influence the proportion of ethylene within bioreactor container 104 include ethylene gas absorbers, such as DeltaTrack™ Model 19005 Mini-Packet Ethylene Gas Absorbers.

Atmospheric control container 104 may include any number of storage chambers 220. For example, atmospheric control container 104 may include one to five storage chambers 220. In the example shown, atmospheric control container 104 includes two storage chambers 220 separated by a common dividing wall 226. Each storage control chamber 220 may be filled with a different atmospheric control material 224 (or mixture of atmospheric control materials). For example, each storage chamber 220 may be filled with an atmospheric control material or combination of materials that affect the proportion of a different component of the atmospheric gas within bioreactor container 104.

Storage chambers 220 may have any configuration that provides sufficient exposure of the contained atmospheric control materials to the ambient gas within bioreactor container 104 to regulate the proportion of one or more components of the ambient gas. For example, storage chambers 220 may include one or more openings 228 that allows the ambient gas to flow into contact with the atmospheric control materials 224 inside. In the illustrated embodiment, each storage chamber has a base 232 and sidewalls 236 which together define a storage volume 240, and an opening 228 in an upper end 242 to allow the ambient gas to flow into the storage volume 240 and contact the atmospheric control materials 224.

Atmospheric control container 216 may be supported by the bioreactor container 104 within bioreactor volume 120, and hold a sufficient volume of atmospheric control materials 224 to last a full growth cycle of the plants. For example, each storage chamber 220 may have a storage volume 240 of between 10 mL and 100 mL, or about 1-5% of the bioreactor volume 120. This may allow the atmospheric control materials 224 to regulate the ambient air within bioreactor container 104 for the duration of the growth cycle, thus allowing bioreactor container 104 to remain sealed for improved plant growth.

Figure 7B:
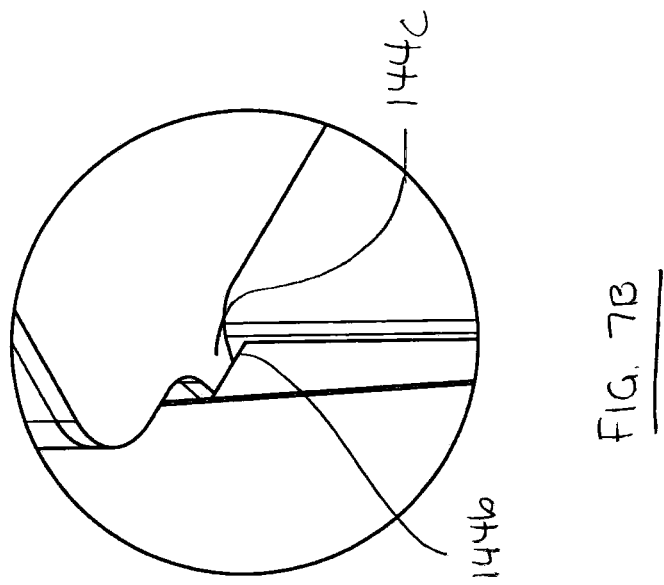
FIG. 7B is an enlargement of region 7B in FIG. 7A.
Figure 7A:
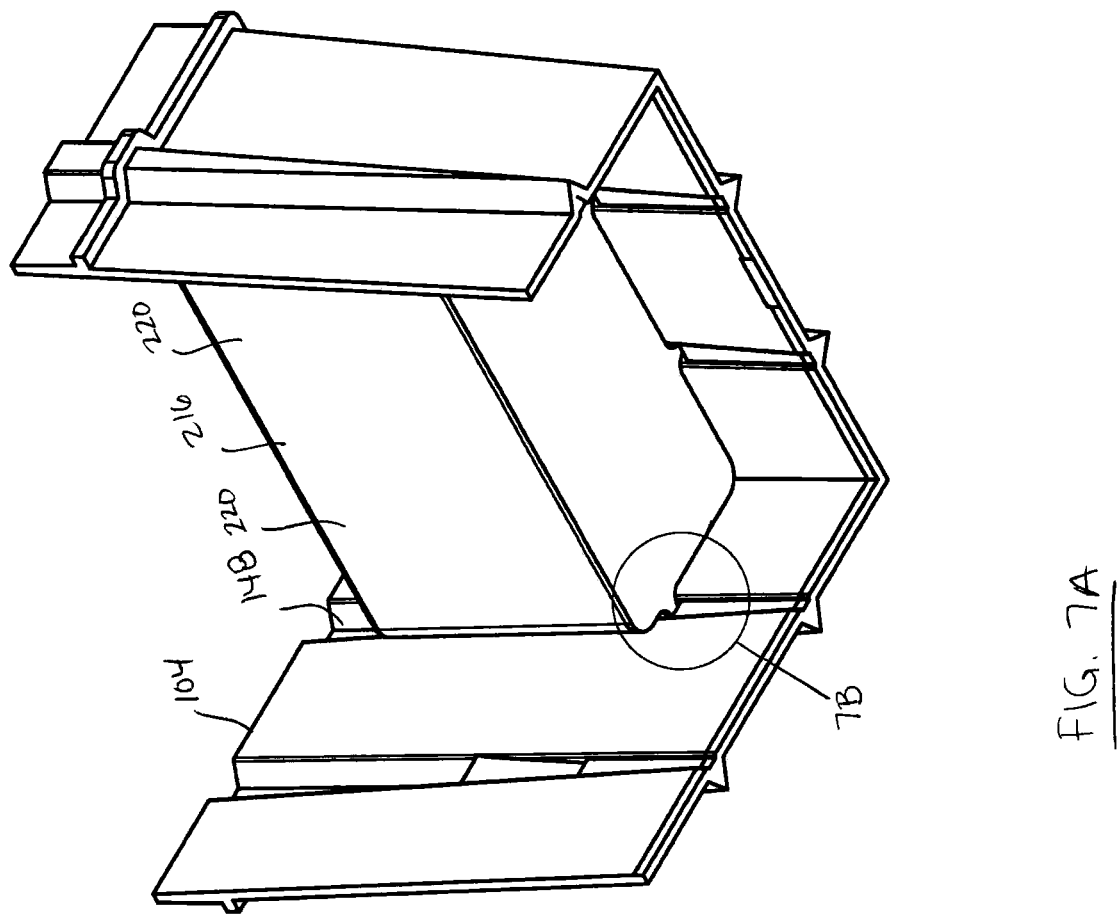
FIG. 7A is a bottom perspective view of the atmospheric control container of FIG. 6A supported in a bioreactor container in which portions of the walls and base have been partially cutaway.

Atmospheric control container 216 may be positioned to hold storage chambers 220 spaced apart from the nutrient medium 188. For example, similar to root stand 128, one or both of atmospheric control container 216 and bioreactor container 104 may include abutment portions 144 which support the storage chambers 220 above the nutrient medium level 136. Referring to FIGS. 7A-7B, abutment portions 144 can take any form suitable for collectively supporting storage chambers 220 above container base 112. In the illustrated embodiment, atmospheric control container 216 includes abutment portions 144c which protrude outwardly from storage chambers 220 and which seat onto abutment portions 144b of container sidewalls 116. As shown, container abutment portions 144b may be formed as shelves having an upper surface that supports abutment portions 144c. Each abutment portion 144c may be situated within a sidewall groove 148. Abutment portions 144c may be sized, shaped, and arranged to key into sidewall grooves 148, which may provide lateral stability and consistent positioning to atmospheric control container 216.

In other embodiments, atmospheric control container 216 may include abutment members formed as legs (not shown) that extend below storage chambers 220 to hold storage chamber 220 above container base 112. In alternative embodiments, atmospheric control container 216 may have walls that are liquid impervious and partially submerged within the nutrient medium in bioreactor container 104.

Figure 8A:
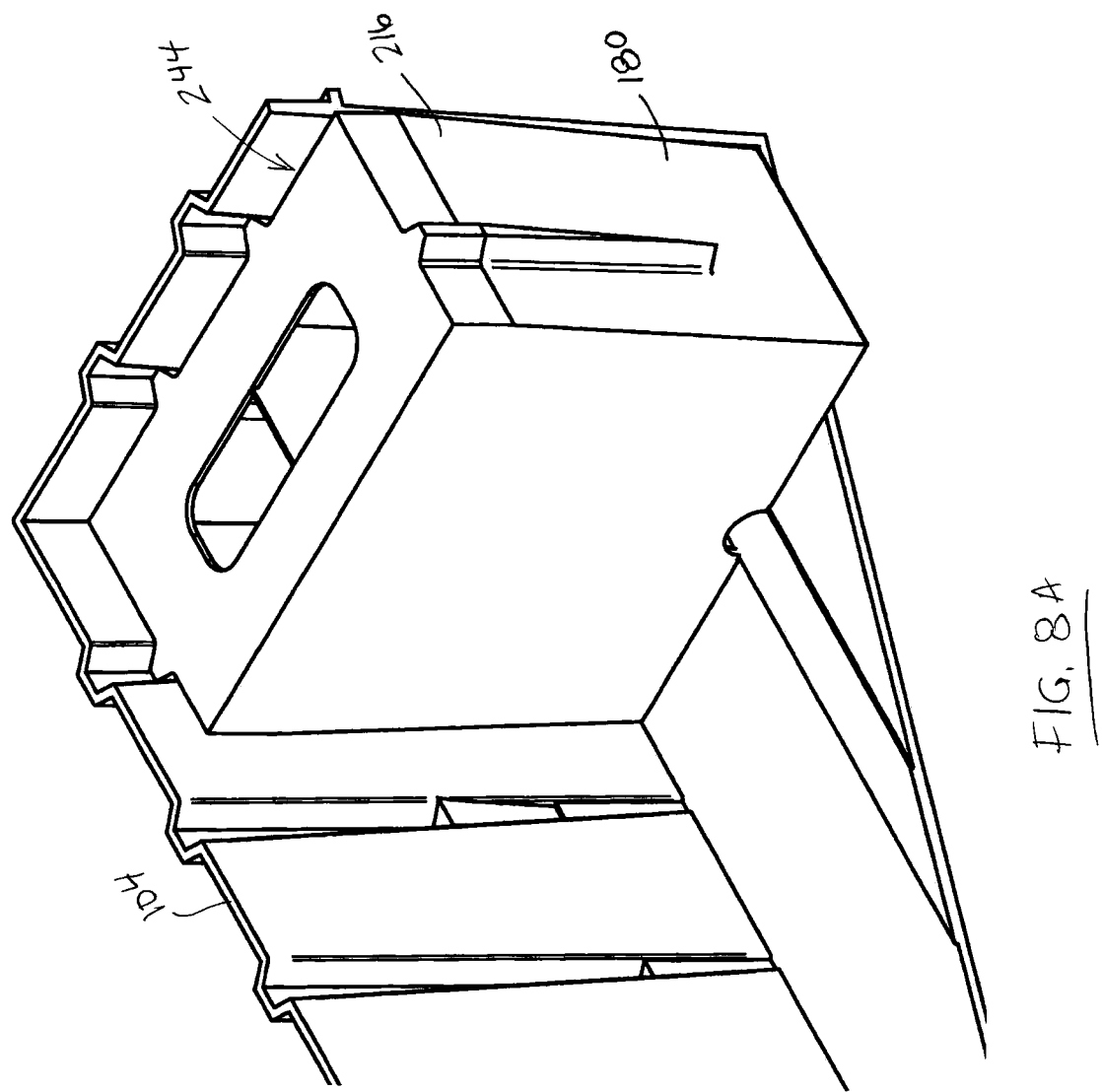
FIG. 8A is a perspective view of a combination gravity well and atmospheric control container in a bioreactor container that has been partially cut-away.
Figure 8B:
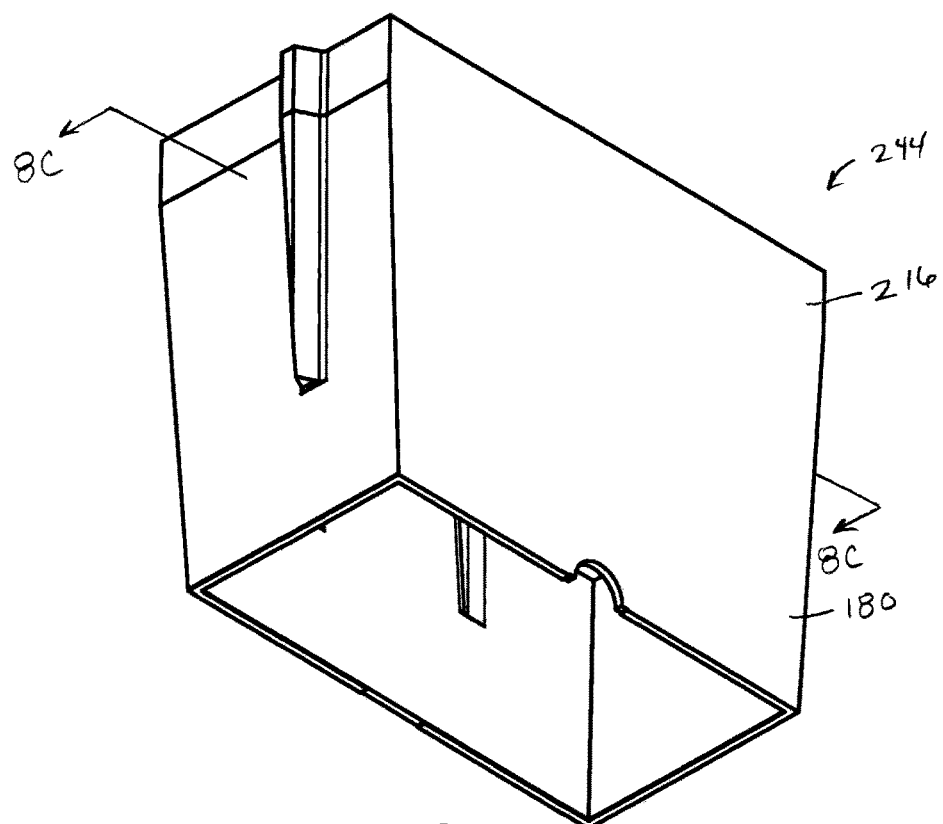
FIG. 8B is a bottom perspective view of the combination gravity well and atmospheric control container of FIG. 8A.
Figure 8C:
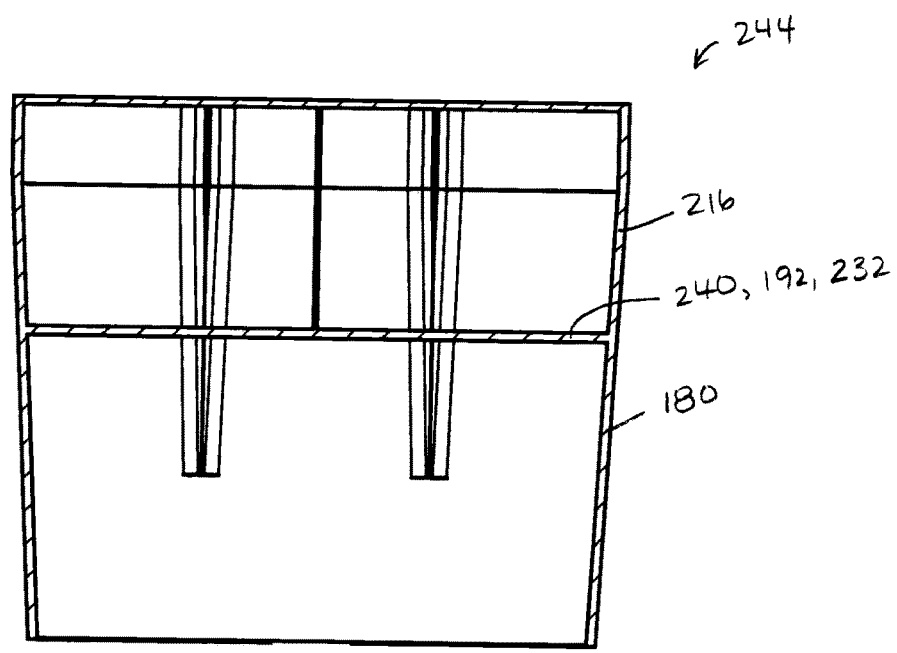
FIG. 8C is a cross-sectional view taken along lines 8C-8C in FIG. 8B.

Reference is now made to FIGS. 8A-8C, which show a combination gravity well 180 and atmospheric control container 216, collectively identified as apparatus 244. As shown, apparatus 244 includes a lower gravity well 180 below an upper atmospheric control container 216. The gravity well 180 and atmospheric control container 216 share a common dividing wall 248, which forms both the gravity well upper wall 192 and the storage chamber bases 232. Apparatus 244 provides a compact arrangement of a gravity well 180 and atmospheric control container 216, which frees up additional space within bioreactor container 104 for growing plants.

Figure 9:
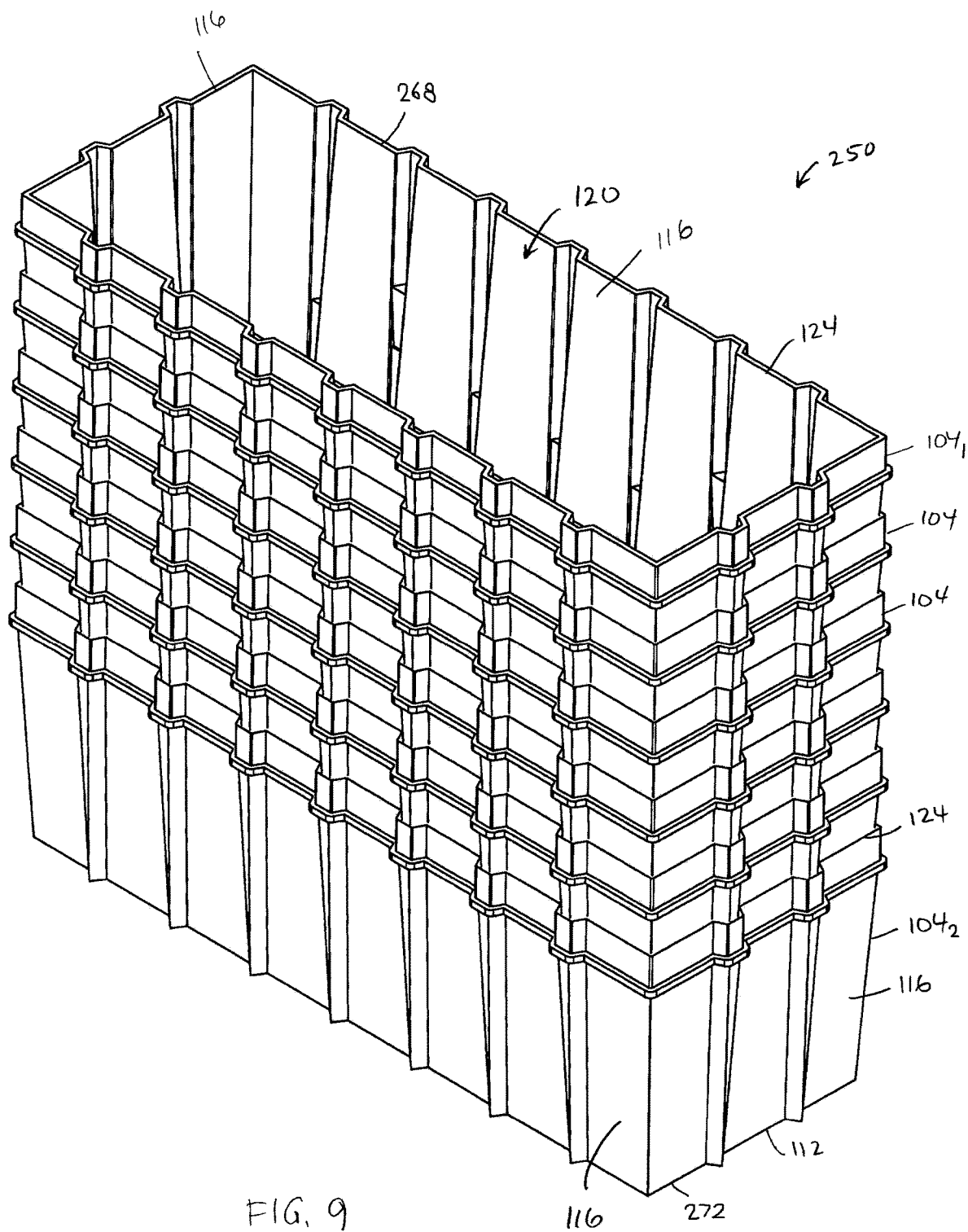
FIG. 9 is a perspective view of a nested stack of bioreactor containers.

Reference is now made to FIG. 9. Between uses of bioreactor containers 104 for growing plants, the bioreactor containers 104 may be sterilized in an autoclave. An autoclave exposes the bioreactor containers 104 to intense heat for a period of time sufficient to kill living matter (e.g. plant matter, bacteria, viruses, etc.). This avoids contamination of the next plant growth cycle, which can impair plant growth.

Autoclaves are large, expensive devices with limited volume capacity. Thus, time and cost can be saved by allowing a greater number of bioreactor containers 104 to be sterilized within a single autoclave. In some embodiments, bioreactor containers 104 have a shape that tapers in width between the container opening 124 and base 112. This allows bioreactor containers 104 to at least partially nest within each other. The nested configuration provides a compact arrangement of bioreactor containers 104 for placement into an autoclave, thereby increasing the number of bioreactor containers 104 that can be simultaneously sterilized. The nested configuration may also provide a compact configuration that may reduce shipping and packaging costs.

Preferably, bioreactor containers 104 are shaped to nest such that at least 50% of a bioreactor can be received inside another bioreactor (i.e. at least 50% of the height of the bioreactor). In the illustrated example, bioreactor containers 104 can receive about 75% of another bioreactor container 104.

In some cases, the container sidewalls 116 of the uppermost bioreactor container 104₁ of the nested stack 250 may tend to deform by deflecting (also referred to as bowing) inwardly in response to the intense heat of the sterilizing process. This is a result of the sidewall material experience some expansion when heated. Such inward bowing may be undesirable, for at least because it may not allow the bioreactor lid 108 (FIG. 1) to properly seal bioreactor volume 120 after sterilizing is completed.

Figure 10A:
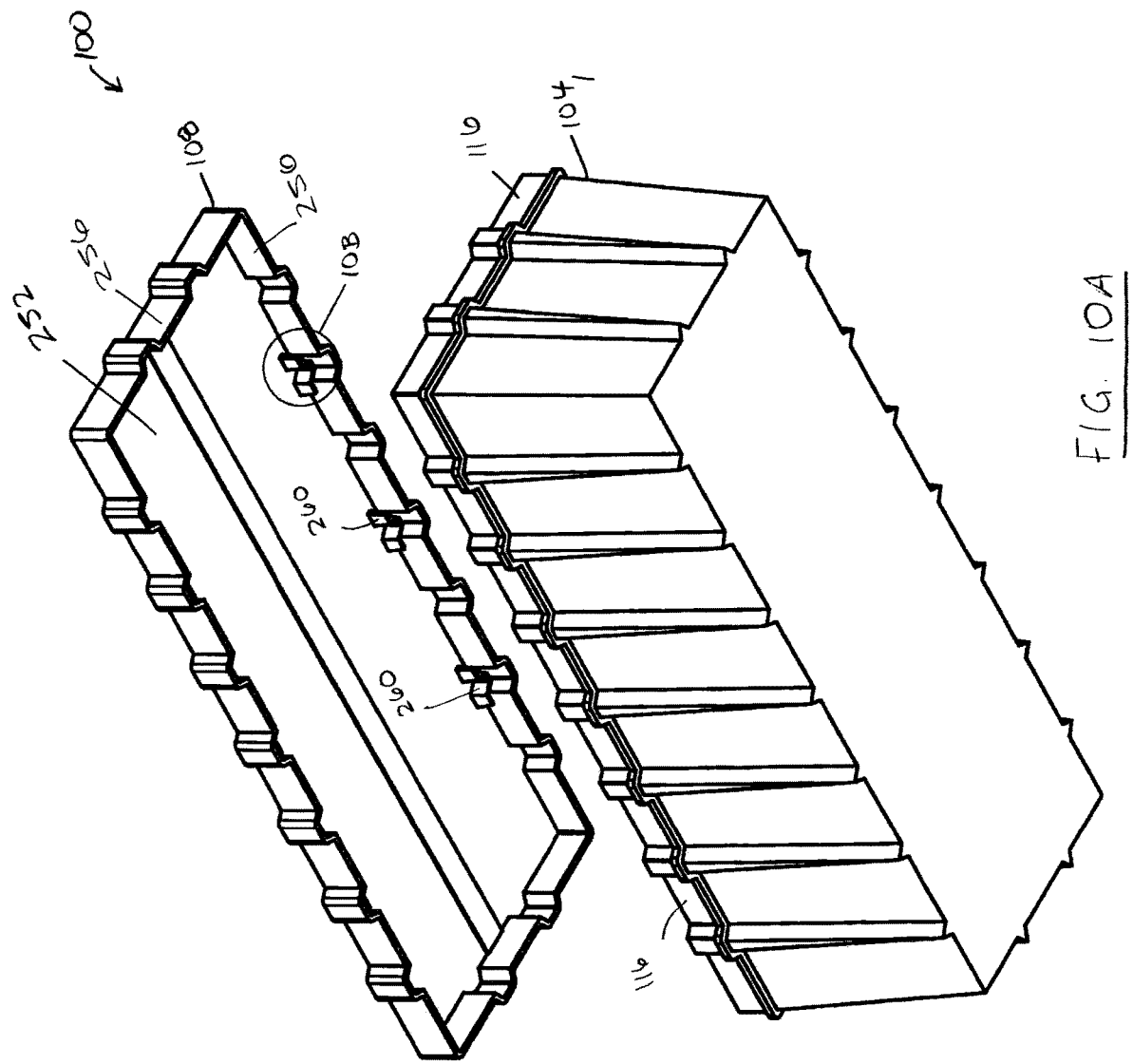
FIG. 10A is a bottom perspective view of the bioreactor of FIG. 1B.
Figure 10C:
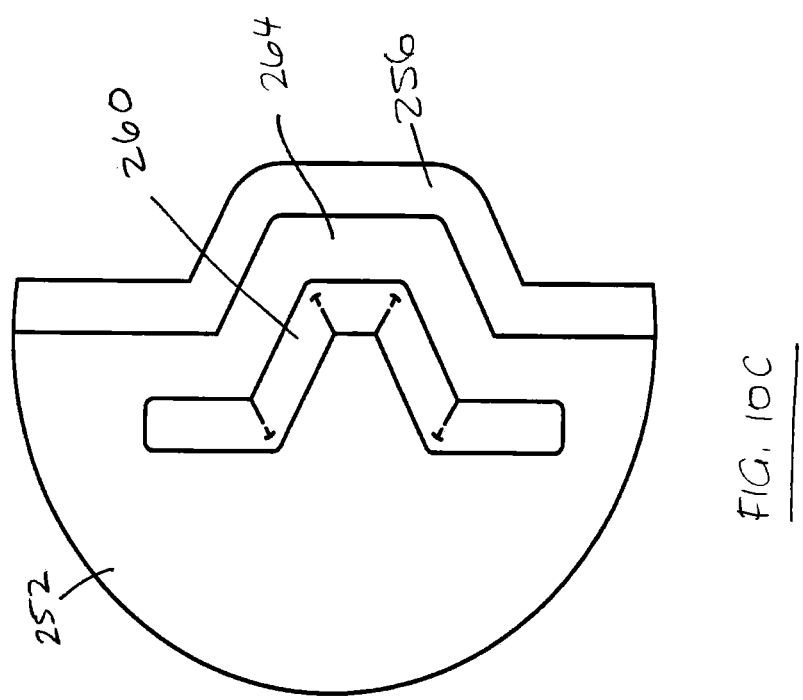
FIG. 10C is a bottom plan view of region 10B of FIG. 10A.
Figure 10B:
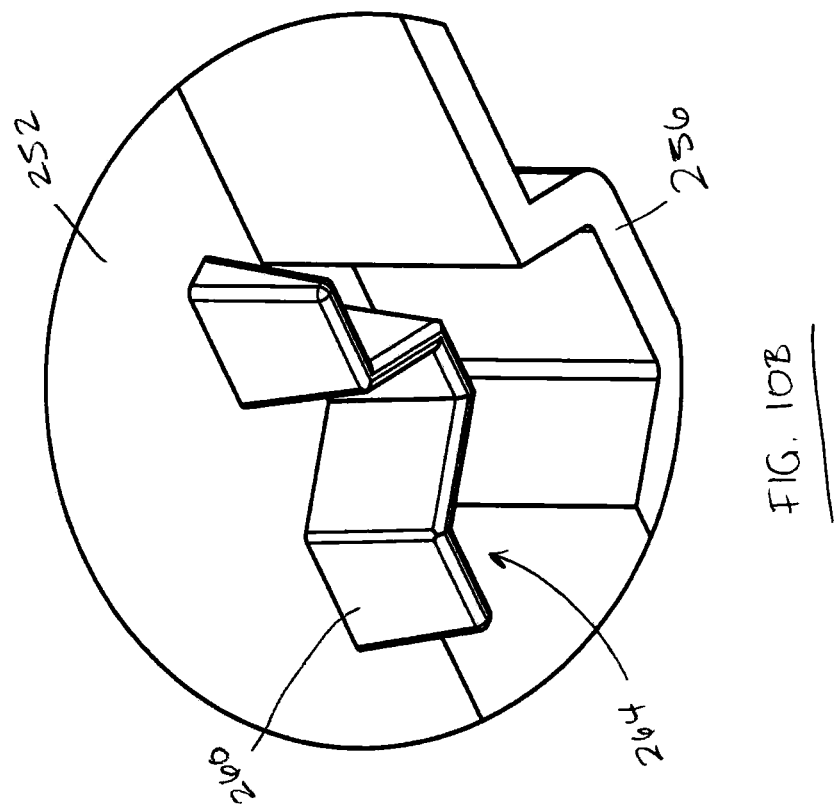
FIG. 10B is an enlargement of region 10B in FIG. 10A.

Reference is now made to FIGS. 10A-10C, in which the uppermost bioreactor container 104₁ of the nested stack 250 (FIG. 9) is shown. In some embodiments, bowing of the container sidewalls 116 may be inhibited by connecting bioreactor lid 108 prior to sterilizing in an autoclave. Bioreactor lid 108 may be configured to inhibit inward and outward deflection of container sidewalls 116 when connected to bioreactor container 104₁. As shown, bioreactor lid 108 may include an upper wall 252, one or more outer sidewalls 256 extending downwardly from upper wall 252, and one or more inner sidewalls 260 extending downwardly from upper wall 252. The inner sidewalls 260 may be spaced apart from the outer sidewalls 256 to define one or more channels 264 that receive portions of container sidewalls 116. Preferably, container sidewalls 116 are receivable into channels 264 with a press-fit (also referred to as a friction fit). When bioreactor lid 108 is connected to bioreactor container 104, the lid inner sidewalls 260 prevent the container sidewalls 116 from deflecting inwardly, and the lid outer sidewalls 256 prevent the container sidewalls 116 from deflecting outwardly.

Lid inner sidewalls 260 may be formed as a plurality of spaced apart (i.e. discontinuous) sidewalls as shown, or a continuously connected sidewall. Similarly, the lid channels 264 may include a plurality of spaced apart (i.e. discontinuous) channels as shown, or one continuously connected channel.

Referring to FIGS. 9 and 10A, the nested stack extends from an upper end 268 (also referred to as the first end 268) defined by the uppermost container $104_1$ (alternatively referred to as the first container $104_1$) to a lower end 272 (also referred to as the second end 272) defined by the lowermost container $104_2$ (alternatively referred to as the second container $104_2$). The second container $104_2$ and each container 104 between the first and second containers $104_1$ and $104_2$ receives at least a portion of another bioreactor container 104 in the stack 250. In use, bioreactor lid 108 may be attached to the first container $104_1$ of stack 250, and then the entire stack 250 of containers 104 with lid 108 may be placed into an autoclave and sterilized. The bioreactor lid 108 may inhibit the sidewalls 116 of the first container $104_1$ from deflecting. The sidewalls of the other containers 104 in the stack may be inhibited from deflecting due to their nested arrangement.

While the above description provides examples of the embodiments, it will be appreciated that some features and/or functions of the described embodiments are susceptible to modification without departing from the spirit and principles of operation of the described embodiments. Accordingly, what has been described above has been intended to be illustrative of the invention and non-limiting and it will be understood by persons skilled in the art that other variants and modifications may be made without departing from the scope of the invention as defined in the claims appended hereto. The scope of the claims should not be limited by the preferred embodiments and examples, but should be given the broadest interpretation consistent with the description as a whole.

The invention claimed is:

1. A bioreactor comprising:
a bioreactor container having a base and one or more container sidewalls connected to the base, the base and container sidewalls together defining an interior bioreactor volume; and
a gravity well supported by the container within the bioreactor volume, the gravity well having an upper wall, one or more gravity well sidewalls extending downwardly from the upper wall, and one or more liquid outlets in the one or more gravity well sidewalls at a lower end of the gravity well, the one or more liquid outlets defining a liquid level of the bioreactor container,
the upper wall and gravity well sidewalls together defining an interior reservoir volume that is sealed except for the one or more liquid outlets.

2. The bioreactor of claim 1, wherein:
the bioreactor container further comprises an openable lid that is connectable to the one or more container sidewalls to seal the interior bioreactor volume in cooperation with the one or more container sidewalls and the base.

3. The bioreactor of claim 1, further comprising:
a root stand supported by the container within the bioreactor volume, the root stand including a root support structure at an elevation above the liquid level defined by the liquid outlet.

4. The bioreactor of claim 3, wherein:
each of the one or more liquid outlets has an upper end located at an elevation below the root support structure.

5. The bioreactor of claim 1, further comprising:
an atmosphere control container supported by the container within the bioreactor volume, the atmosphere control container including two or more storage chambers for holding atmospheric control materials.

* * * * *